United States Patent [19]

Laue et al.

[11] Patent Number: 5,710,339
[45] Date of Patent: Jan. 20, 1998

[54] BISPHOSPHINES AS CATALYSTS FOR ASYMMETRIC REACTIONS

[75] Inventors: Christian Laue, Monheim; Georg Schröder, Leverkusen; Dieter Arlt, Köln, all of Germany

[73] Assignee: Bayer Aktiengesellschaft, Leverkusen, Germany

[21] Appl. No.: 664,073

[22] Filed: Jun. 13, 1996

[30] Foreign Application Priority Data

Jun. 20, 1995 [DE] Germany ............. 195 22 293.8

[51] Int. Cl.$^6$ ...................................... C07F 9/50
[52] U.S. Cl. ...................................... 568/16; 568/17
[58] Field of Search ........................... 568/17, 16

[56] References Cited

U.S. PATENT DOCUMENTS

| | | | |
|---|---|---|---|
| 4,556,740 | 12/1985 | Hansen et al. | 568/13 |
| 4,691,037 | 9/1987 | Yoshikawa et al. | 556/18 |
| 5,510,503 | 4/1996 | Laue et al. | 556/21 |

FOREIGN PATENT DOCUMENTS

| | | |
|---|---|---|
| 0 104 375 A1 | 4/1984 | European Pat. Off. |
| 0 245 959 A3 | 11/1987 | European Pat. Off. |
| 0 256 634 A3 | 2/1988 | European Pat. Off. |
| 0 272 787 A3 | 6/1988 | European Pat. Off. |
| 0 366 390 A2 | 5/1990 | European Pat. Off. |
| 0 398 132 A3 | 11/1990 | European Pat. Off. |
| 0 470 756 A2 | 2/1992 | European Pat. Off. |
| 0 643 065 A1 | 3/1995 | European Pat. Off. |
| 204279 | 5/1988 | Hungary . |

OTHER PUBLICATIONS

R. Noyori, J. Am. Chem. Soc., vol. 109, pp. 5856–5858 (1987).
T. Manimara, Organometallics vol. 12, pp. 1467–1470 (1993).
T. Ikariya et al, J. Chem. Soc. Chem. Commun., pp. 922–927 (1985).
R. Schmid, Helevtica Chemica Acta, vol. 74, pp. 370–389 (1991).
M. Murata et al., SYNLETT, pp. 827–829 (Nov. 1991).

*Primary Examiner*—C. Warren Ivy
*Assistant Examiner*—Jean F. Vollano
*Attorney, Agent, or Firm*—Sprung Kramer Schaefer & Briscoe

[57] ABSTRACT

The invention relates to enantiomerically pure bisphosphines of the general formula (I)

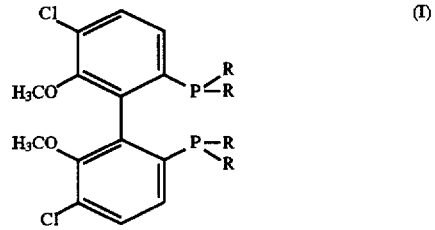

where
R is as defined in the description,
a process for their preparation and their use in metal complexes as catalysts for asymmetric reactions, in particular asymmetric hydrogenations.

6 Claims, No Drawings

BISPHOSPHINES AS CATALYSTS FOR ASYMMETRIC REACTIONS

The invention relates to new enantiomerically pure bisphosphines, a process for their preparation and their use in metal complexes as catalysts for asymmetric reactions, in particular asymmetric hydrogenations.

It is already known that complexes of certain bisphosphines with metals of group VIII of the Periodic Table can be used for asymmetric hydrogenations and enantioselective hydrogen shifts (cf. R. Schmid et al. Helv. Chim. Acta, 74, 370 (1991)).

EP A 104 375 claims a bisphosphine which is distinguished from the phosphines of the invention by it having a fluorine atom in place of the chlorine atom. However, it was to be assumed from these known fluorine compounds that they would, owing to the high electronegativity of the fluorine, have a similarly poor reactivity as BIFUP, which is provided with electronegative substituents (K. Achiwa Synlett, 1991, 827). It is stated there on page 828 (see also Table 1) that the ligand gives only poor conversion, owing to the electronegative groups. The stereoselectivity is also worse; i.e. the proportion of the minor component rose from <0.5%, which is achieved by other bisphosphines known hitherto, to 2.5% (=95% e.e.).

The ligand of the invention now has the halogen chlorine in this position in place of the halogen fluorine and shows, e.g. in the form of Ru complexes in the hydrogenation of methyl acetoacetate, very good selectivities of >99% e.e., which was not to be expected in view of the above prejudice.

Furthermore, for example, the ligands of the, invention are able, in the form of their ruthenium complexes, to catalyze the hydrogenation of 2-(3-benzylphenyl)-propenoic acid to be the corresponding propanoic acid (=S-ketoprofen derivative) with high selectivity.

DE 4 330 730 A1 has already described ligands which give a selectivity of 88% e.e. in the hydrogenation of the above propenoic acid derivatives. However, the ligands used there give only poor enantiomer purities when resolved into the enantiomers by crystallization, which is why, as described in the above patent, the complicated racemate resolution by chromatography is advised for obtaining chiral phases. In contrast, the ligands of the invention can easily be resolved into the enantiomers by crystallization.

The invention provides enantiomerically pure bisphosphines of the general formula (I)

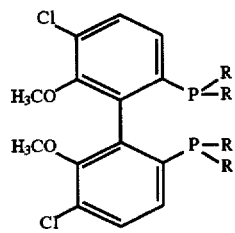

where
R in each case represents a phenyl group which in turn can be substituted by from 1 to 3 substituents from the group $OR^1$, $R^1$, nitro, $NH_2$, $NHR^1$ or $NR_2^1$, where $R^1$ is an alkyl group having up to 6, preferably up to 4, carbon atoms, or
R is an alkyl group having up to 7, preferably up to 4, carbon atoms or a cycloalkyl group having from 3 to 7, preferably 5 or 6, carbon atoms.

Particular preference is given to enantiomerically pure bisphosphines of the general formula (I) in which R is phenyl.

The bisphosphines of the general formula (I) can be prepared by a) reacting 5-Br-2-Cl-anisole with phosphorus oxychlorides of the general formula (II)

where
R is as defined above,
by customary methods after a selective monometallation of bromo-chloro-anisole, preferably by means of a Grignard reaction, to give compounds of the general formula (III)

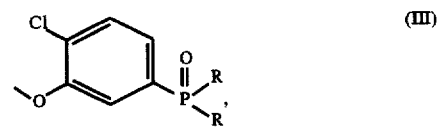

where
R is as defined above,
and metallating this in the 6-position by ortho-metallation methods, preferably using lithium amide, and subsequently reacting it with iodine to give compounds of the general formula (IV)

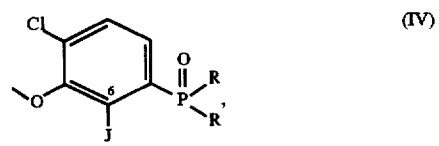

where
R is as defined above,
and subsequently dimerizing this by customary methods to give racemic compounds of the general formula (V)

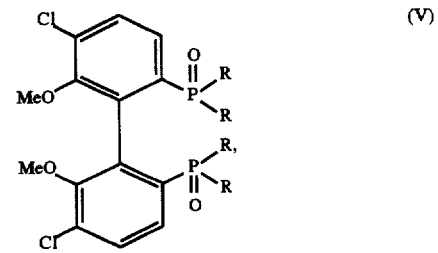

where
R is as defined above,
and resolving these phosphine oxides into their enantiomers by crystallization with enantiomerically pure monocarboxylic or dicarboxylic acids and reducing the resolved enantiomers to give compounds of the formula (I), or b) by alternatively preparing compounds of the general formula (III) by metallating 5-Br-2-Cl-anisole, e.g. via the mono-Grignard reagent, then reacting it with phosphine chlorides of the general formula (VI)

where
R is as defined above,
and subsequently oxidizing the product by customary methods.

The novel bisphosphines of the formula (I) form complexes with transition metals such as metals of group VIII.

in particular ruthenium, rhodium and iridium, which can be used as catalysts in asymmetric hydrogenations and also for enantioselective hydrogen shifts in prochiral, allylic systems. In the hydrogenations mentioned, preference is given to ruthenium, iridium and rhodium complexes, while for isomerizations preference is given to rhodium complexes. These catalysts, i.e. the complexes comprising a metal of group VIII and the phosphorus compounds of the formula (I) are new and are likewise subject-matter of the present invention.

The complexes in question can be prepared in a manner known per se, for example by reacting a compound of the formula (I) in a suitable, inert organic or aqueous solvent with a compound able to donate a metal of group VIII. Examples of suitable, e.g. rhodium-donating compounds which might be mentioned are organic rhodium complexes with ethylene; propylene and the like, and also with bisolefins, e.g. 1,5-cyclooctadiene, 1,5-hexadiene, bicyclo [2.2.1]hepta-2,5-diene or with further dienes which form readily soluble rhodium complexes.

Preferred rhodium-donating compounds are, for example, di-chloro-bis(1,5-cyclooctadiene)dirhodium, di-chloro-bis (norbornadiene)dirhodium, bis(1,5-cyclooctadiene) rhodium-tetrafluoroborate or bis(cyclooctadiene)rhodium perchlorate. An example of an iridium-donating compound which might be mentioned is di-chloro-bis(1,5-cyclooctadiene)diiridium.

Of particular interest are ruthenium complexes with bisphosphines of the general formula (I). Typical examples which might be mentioned but are not a restriction are the ruthenium complexes of the formulae (VII) to (XIII) below.

EXAMPLES OF TYPICAL RUTHENIUM COMPLEXES

| | |
|---|---|
| $Ru_2Cl_4B_2(S)$ | (VII) |
| $[Ru\ Hal\ Q\ B]^{\oplus}Y^{\ominus}$ | (VIII) |
| $Ru\ B_n\ OOCR^3OOCR^4$ | (IX) |
| $[RU\ H_xB_4]^{l m \oplus}Y_m^{\bullet}$ | (X) |
| $[Ru\ Hal\ (PR^5{}_2R^6)B]^{(2+)}\ Hal_2^{\bullet}$ | (XI) |
| $[Ru\ H\ Hal\ B_2]$ | (XII) |
| $[B\ Ru\ (acac)_2]$ | (XIII) |
| $[B\ Ru\ Y_2]$ | (XIV) | where:
acac is acetylacetonate
B represents a bisphosphine of the general formula (I),
Hal represents halogen, in particular iodine, chlorine or bromine,
$R^3$ and $R^4$ are identical or different and represent alkyl having up to 9 carbon atoms, preferably up to 4 carbon atoms, which is optionally substituted by halogen, in particular fluorine, chlorine or bromine, or represent phenyl, which is optionally substituted by alkyl having from 1 to 4 carbon atoms, or represent an α-aminoalkyl acid preferably having up to 4 carbon atoms,
or together form an alkylidene group having up to 4 carbon atoms,
$R^5$ and $R^6$ are identical or different and represent optionally substituted phenyl, preferably substituted by alkyl having from 1 to 4 carbon atoms or halogen,
Y represents Cl, Br, J, $ClO_4$, $BF_4$ or $PF_6$,
Q represents an unsubstituted or substituted benzene ring such as p-cymene,
S represents a tertiary amine such as triethylamine, tri-n-butylamine or pyridine,
n and m each represent 1 or 2,
x represents 0 or 1, where, in formula (X), n represents 1 and m represents 2 when x=0, and n represents 2 and m represents 1 when x=1.

The complexes of the formulae (VII) to (XIII) can be prepared by methods known per se.

The complexes of the formulae (VII) and (XII) can be prepared, for example, in a manner similar to the processes described in EP-174 057 or in Chem. Comm. 922 (1985).

The complexes of the general formula (VIII) are obtained, for example, by reaction of known ruthenium complexes $[RuHal_2Q]_2$ with bisphosphines of the general formula (I) in inert organic solvents as described, for example, in EP 366 390.

Complexes of the general formula (IX), n=1, can be obtained, for example, by processes indicated in EP 245 959, by reacting complexes of the general formula (VII) with appropriate carboxylic acids, preferably in alcoholic solvents.

Complexes of the formulae (IX), n=2, and where n=1 and $R^3$, $R^4$=$CF_3$ can be prepared by the processes indicated in EP 272 787.

The complexes of the general formula (X) can be prepared by a method similar to the process described in EP-256 634.

The complexes of the general formula (XI) can be prepared by a method similar to the process described in EP-470 756 by reacting the Ru precursors described there with the novel bisphosphines of the general formula (I).

Complexes of the formula (XIII) can be prepared by a method similar to the processes indicated in P. Stahly et al., Organometallics 1993, 1467 ff.

Complexes of the formula (XIV) can be prepared by a method similar to the processes indicated in J. A. C. S. 1987, 109, 5856 to 5858.

The bisphosphines of the invention in the form of their complexes with metals of group VIII and, in particular, with ruthenium can be used for asymmetric hydrogenations. Suitable substrates are substituted or unsubstituted α- or β-ketoesters or α-or β-keto-amides, α-or β-amino or α-or β-hydroxy-ketones and acetamidocinnamic acid derivatives.

Also suitable are acrylic acids, in particular 2-arylpropenoic acids such as 2-(6'-methoxy-2'-naphthyl)-propenoic acid, 2-(4-isobutyl)-propenoic acid and 2-(3-benzylphenyl)-propenoic acid and their salts, for example with tertiary amines.

In carrying out such hydrogenations, these complexes can first be prepared and then added to a solution of the substance to be hydrogenated. However, as an alternative, they can also be prepared in situ, e.g. in the presence of a substance to be hydrogenated.

The asymmetric hydrogenation can be carried out in a suitable organic solvent which is inert under the reaction conditions. Solvents of this type which may be mentioned in particular are lower alcohols such as methanol or ethanol, or mixtures of such alcohols with halogenated hydrocarbons such as methylene chloride, chloroform and the like, or with cyclic ethers such as tetrahydrofuran or dioxane, and the like.

The ratio of metals to bisphosphines of the general formula (I) is advantageously between about 0.5 and about 2 mol, preferably about 1 mol of ruthenium, per mol of bisphosphine ligand. The ratio of metal in the complexes to the substances to be hydrogenated is advantageously between about 0.0005 and 1 mol %, preferably between about 0.005 and 0.6 mol %.

The asymmetric hydrogenation using the complexes of the invention is advantageously carried out at a temperature of from about 0° C. to about 100° C., depending on the substrate used. This hydrogenation is also advantageously carried out under pressure, preferably at a pressure of from about 5 to about 200 bar, particularly preferably from about 40 to about 140 bar.

Furthermore, the bisphosphine complexes of the invention can be used as catalyst for enantioselective hydrogen shifts in prochiral allylic systems. They are of particular interest, for example, in connection with the preparation of optically active compounds of the general formula (XV)

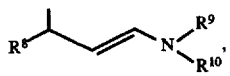  (XV)

where
$R^8$ is protected hydroxymethyl or a radical of the formula

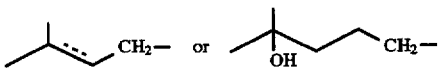

where the broken line can represent an additional bond, and
$R^9$ and $R^{10}$ are identical or different and are lower alkyl (1–7 carbon atoms), starting from compounds of the general formula (XVI)

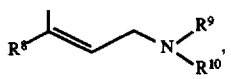  (XVI)

where
$R^8$, $R^9$ and $R^{10}$ are as defined above.

The compounds (XV) or the aldehydes obtained therefrom by hydrolysis, and also the acids and alcohols derived from these aldehydes, are of interest, for example, as intermediates in the synthesis of the side chains of vitamins E and $K_1$.

To carry out the hydrogen shires mentioned, the phosphorus compounds of the formula (I) can be brought into contact as such with a, for example, rhodium- or iridium-donating compound in a solution of a compound to be treated. Alternatively, the phosphorus compounds of the formula (I) can first be reacted in a suitable solvent with a, for example, rhodium-or iridium-donating compound to give the corresponding catalyst complex, and this can then be added to a solution of a compound to be treated, with the latter method being preferred.

Both the reaction of the phosphorus compounds of the formula (I) with a, for example, rhodium- or iridium-donating compound and the hydrogen shifts mentioned can be carried out in suitable organic solvents which are inert under the reaction conditions. Solvents of this type which may be mentioned in particular are lower alkanols such as methanol or ethanol, aromatic hydrocarbons such as benzene or toluene, cyclic ethers such as tetrahydrofuran or dioxane, esters such as ethyl acetate, or mixtures thereof, and the like. Furthermore, the complex formations can also be carried out in aqueous medium or in dichloromethane.

The ratio of, for example, rhodium or iridium to the ligands of the formula (I) is advantageously between about 0.05 and about 5 mol, preferably between about 0.5 and about 2 mol, of metal per mol of ligand of the formula (I).

The amount of metal in the complexes containing the ligands of the formula (I), based on the compounds to be treated for the purpose of effecting a hydrogen shift, is preferably between about 0.005 and about 0.5 mol %, in particular between about 0.01 and about 0.2 mol %.

The hydrogen shifts mentioned using metal complexes containing the ligands of the formula (I) can advantageously be carried out in an inert organic solvent and at a temperature from about room temperature to about 130° C. This reaction is preferably carried out at elevated temperature, i.e. depending on the solvent used, either at reflux temperature of the reaction mixture or in a closed vessel under pressure.

Experimental part:

Abbreviations used in the following are:
cym: 4-isopropyltoluene
THF: tetrahydrofuran
DMF: dimethylformamide
TBME: tert-butyl methyl ether
HPLC: high pressure liquid chromatography
LDA: lithium diisopropyl-amide A) Preparation of the bisphosphines 1a) Diphenyl-(4-chloro-3-methoxy-phenyl)-phosphine oxide (formula III)

9.05 g of Mg turnings are heated under argon with a spatula tip of iodine until iodine vapours are formed and the mixture is stirred dry for 5 minutes. 350 ml of THF (analytical reagent) are subsequently added and the mixture is heated to the boiling point. 75 g of 5-bromo-2-chloro-anisole in 360 ml of THF are added under reflux over ½ hour, making sure that the reaction has started on addition of the first amounts. Stirring is continued under reflux for 40 minutes.

The mixture is cooled to 0° C. and 88.5 g of diphenylphosphinic chloride in 450 ml of THF are added dropwise at from 0° to 5° C. over 25 minutes with ice cooling. The mixture is stirred for 2 hours at room temperature. At from 0° to 15° C., 450 ml of 1N HCl are added dropwise over 15 minutes and the mixture is stirred well for 15 minutes. The organic phase is separated off and the aqueous phase is extracted twice with 0.5 l each time of methylene chloride and the combined organic phases are washed with 0.5 l each of 1N NaOH, Water and saturated NaCl solution, dried with $MgSO_4$ and evaporated. 120 g of crude product are stirred with 400 ml of TBME, evaporated at room temperature to about 150 ml, stirred for 2 hours and filtered.

Yield: 81 g (70% yield)
m.p.: 104° to 107° C.

1b) Diphenyl-(4-chloro-3-methoxy-phenyl)-phosphine oxide (formula (III))

1.31 g of Mg turning are heated under argon with a spatula tip of iodine using hot air until iodine vapours are formed and the mixture is stirred dry for 5 minutes. 50 ml of THF are subsequently added and the mixture is heated to the boiling point. 10 g of 5-bromo-2-chloro-anisole in 50 ml of THF are added under reflux over ½ hour, making sure that the reaction has started on addition of the first amounts. Stirring is continued for 40 minutes under reflux.

The mixture is cooled to 0° C. and 9.9 g of diphenylphosphinic chloride in 50 ml of THF are added dropwise at from 0° to 5° C. over 25 minutes with ice cooling. The mixture is stirred for 2 hours at room temperature. While cooling 2.8 g of methanol are added and the mixture is evaporated to dryness on a rotary evaporator. The residue is taken up in 200 l of acetone and 13.1 g of aqueous hydrogen peroxide solution is added. After stirring for 45 minutes at room temperature and adding 200 ml of water and 135 ml of saturated aqueous sodium dithionite solution, the acetone is removed in vacuo and the remaining solution is extracted with methylene chloride. The organic phase is subsequently extracted with water, saturated NaCl solution, dried with MgSO$_4$ and evaporated. The residue is stirred with TBME at 0° C. and filtered.

Yield: 5.91 g (40%)
m.p.: 104° to 107° C.

2) Diphenyl-(2-iodo-4-chloro-3-methoxy-phenyl)-phosphine oxide (formula (IV))

112 ml of a 2M solution of LDA in THF are added at −70° C. over 5 minutes to a solution of 64.2 g of diphenyl-(4-chloro-3-methoxy-phenyl)-phosphine oxide in 930 ml of THF. The solution is warmed to 0° C. and left at this temperature for 5 minutes. Subsequently, at −76° C., a solution of 56.8 g of I$_2$ in 670 ml of THF is added dropwise over 75 minutes, the mixture is stirred for a further 5 minutes at this temperature, warmed to room temperature over 45 minutes and stirred further for 1 hour at this temperature.

For the work-up, 320 ml of Na$_2$SO$_3$ solution and 200 ml of water are added and the mixture is extracted with ethyl acetate. The organic phase is washed with saturated NaCl solution, dried with MgSO$_4$ and freed of the solvent.

Crude yield: 90.6 g (103% by weight)
Purity according to $^1$H-NMR: about 70%

3) rac-(5,5'-Dichloro-6,6'-dimethoxy-biphenyl-2,2'-diyl)-bis-(diphenylphosphine oxide) (formula (V))

A mixture of 90.5 g of crude diphenyl-(2-iodo-4-chloro-3-methoxy-phenyl)-phosphine oxide and 37.1 g of Cu powder are boiled with 395 ml of DMF for 16 hours at 140° C. under argon. The mixture is filtered hot under suction through a glass frit and washed with a total of about 100 ml of warm DMF. The filtrate is freed of the solvent and stirred with 900 ml of TBME.

Yield: 39.1 g
m.p.: 175° C. (decomposition)

4) (−)-(5,5'-dichloro-6,6'-dimethoxy-biphenyl-2,2'-diyl)-bis-(diphenyl-phosphine oxide (formula (V))

A solution of 7.07 g of anhydrous (−)-dibenzoyltartaric acid in 110 ml of ethyl acetate is added dropwise at room temperature to a solution of 13.5 g of (5,5'-dichloro-6,6'-dimethoxy-biphenyl-2,2'-diyl)-bis-(diphenyl-phosphine oxide) in 200 ml of methylene chloride. The resulting suspension is stirred overnight and filtered. The residue is dried and the filtrate is freed of the solvent.

Crude weight of salt, crystals: 8.05 g (39% by weight)
Crude weight of salt, filtrate: 11.61 g (56% by weight)

The crystals were taken up in 100 ml of methylene chloride and extracted twice with 25 ml each time of 1N NaOH solution. The organic phase is extracted with 1N HCl, 1N NaOH and saturated NaCl solution and dried with MgSO$_4$.

Yield of crystals after work-up: 5.33 g (39% yield)
Enantiomeric purity: 99.4% e.e.

The enantiomeric purity is determined by analytical HPLC.
n-heptane/THF 1:1 is used as eluent.

$[\alpha]_D = -99.7$ (c=1, DMF)
m.p.: 179° C.

5) (+)-(5,5'Dichloro-6,6'-dimethoxy-biphenyl-2,2'-diyl)-bis-(diphenylphosphine oxide) (formula V)

The filtrate obtained under 4) is evaporated and worked up by a method similar to the work-up of the crystals under 4).

Yield of filtrate after work-up: 7.2 g (53% yield)
Enantiomeric purity according to HPLC: 84.1% e.e.

A solution of 3.5 g of anhydrous (+)-dibenzoyltartaric acid in 59 ml of ethyl acetate is added dropwise at room temperature to a solution of 7.0 g crude worked-up filtrate of (−)-(5,5'-dichloro-6,6'-dimethoxy-biphenyl-2,2'-diyl)-bis-(diphenyl-phosphine oxide) in 104 ml of methylene chloride. The suspension formed is stirred overnight and filtered. The residue is dried and the filtrate is freed of the solvent.

A crude weight of salt, crystals: 7.85 g (38% based on rac-(5,5'-dichloro-6,6'-dimethoxy-biphenyl-2,2'-diyl)-bis-(diphenyl-phosphine oxide)
Crude weight of salt, filtrate: 2.84 g The crystals are worked up as described above.
Yield of crystals after work-up: 5.17 g (38% based on rac-(5,5'-dichloro-6,6'-dimethoxy-biphenyl-2,2'-diyl)-bis-(diphenyl-phosphine oxide)
Enantiomeric purity: >99.9% e.e. (by HPLC)
m.p.: 176° C. $[\alpha]_D = +104.1$(C=1, DMF)

6) (+)-(5,5'-Dicholor-6,6'-dimethoxy-biphenyl-2,2'-diyl)-bis-(diphenyl-phosphine) (formula (I))

5.06 g of (+)-(5,5'-dichloro-6,6'-dimethoxy-biphenyl-2,2'-diyl)-bis-(diphenyl-phosphine oxide) are boiled under reflux in a mixture of 195 ml of xylene, 35.8 ml of absolute tributylamine and 9.1 ml of trichlorosilane for 2.5 hours. For the work-up, the mixture is slowly admixed while cooling with 72 ml of 30% strength aqueous NaOH, the organic phase is separated off and the aqueous phase is then extracted with 75 ml of TBME. The organic phases are extracted with water and saturated NaCl solution, dried with MgSO$_4$ and freed of the solvent. The residue is stirred with 65 ml of ethanol and filtered.

Yield: 4.0 g (84%)
m.p.: 220° to 223° C. (decomp.)
$[\alpha]_D = +55.1$(c=1, CHCl$_3$)
Enantiomeric excess: >99.9% (by HPLC)

7) (−)-(5,5'-Dichloro-6,6'-dimethoxy-biphenyl-2,2'-diyl)-bis-(diphenyl-phosphine) (formula (I))

2.35 g of (−)-(5,5'-dichloro-6,6'-dimethoxy-biphenyl-2,2'-diyl)-bis-(diphenyl-phosphine oxide) are reacted using a method similar to 6).

Yield: 1.78 g (80%)
$[\alpha]_D = -50.7$ (c=1, CHCl$_3$)
m.p.: 223° to 225° C.
Enantiomeric excess: >99.9% (by HPLC)

B) Reference example from DE 4 330 730

1a) Racemate resolution of (bis-4,4'-dibenzofuran-3-yl)-diphenylphosphine oxide by crystallization A solution of 358 mg of anhydrous (−)-dibenzoyltartaric acid in 29 ml of ethyl acetate is added dropwise at room temperature to a solution of 735 mg of(bis-4,4'-dibenzofuran-3-yl)-diphenylphosphine oxide in 44 ml of chloroform and the mixture is heated under reflux for 30 minutes. It is subsequently stirred for 48 hours at room temperature and filtered. The residue is dried and the filtrate is freed of the solvent.

The crystals are taken up in 5 ml of methylene chloride and extracted twice with about 3 ml each time of 1N NaOH solution. The organic phase is extracted with 1N HCl,1N NaOH, saturated NaCl solution and dried with MgSO$_4$.

Yield of crystals after work-up: 47 mg
Enantiomeric purity: 5% e.e. (according to HPLC)

1b) A solution of 244 mg of anhydrous (−)-dibenzoyltartaric acid in 3.8 ml of ethyl acetate is added dropwise at room temperature to a solution of 500 mg of (bis-4,4'-dibenzofuran-3-yl)-diphenylphosphine oxide in 7.5 ml of methylene chloride. The mixture is subsequently stirred for 48 hours at room temperature and filtered. The residue is dried and the filtrate is freed of the solvent.

The crystals are taken up in 5 ml of methylene chloride and extracted twice with about 3 ml each time of 1N NaOH solution. The organic phase is extracted with 1N HCl, 1N NaOH and saturated NaCl solution and dried with $MgSO_4$.

Yield of crystals after work-up: 174 mg
Enantiomeric purity: 5% e.e. (according to HPLC)

C) Preparation of the catalyst complexes

1) [Iodo-Ru-cym-((+)-5,5'-dichloro-6,6'-dimethoxy-biphenyl-2,2'-diyl)-bis-diphenylphosphine]iodide A solution of 42 mg of $(cym_2Ru_2I_4)$ in 5 ml of methanol/methylene chloride (1:1) is added to a mixture of 61 mg of((+)-5,5'-dichloro-6,6'-dimethoxy-biphenyl-2,2'-diyl)-bis-diphenylphosphine in 5 ml of methanol/methylene chloride (1:1), the mixture is boiled for 10 minutes under reflux with exclusion of air and evaporated.

$^{31}$P-NMR $(CDCl_3)$:41.3(d,J=61.5 ppm),25.2(d,J=61.5 ppm)

[(+)-(5,5'Dichloro-6,6'-dimethoxy-biphenyl-2,2'-diyl)-bis-diphenylphosphine)$_2Ru_2Cl_4$]NEt$_3$ A mixture of 23.5 m g of dichloro-cycloocta-1,5-diene-ruthenium-(II), 61 mg of ((+)-5,5'-dichloro-6,6'-dimethoxy-biphenyl-2,2'-diyl)-bis-diphenylphosphine, 0.035 ml of triethylamine and 3 ml of toluene is stirred for 10 hours at 120° C. with exclusion of air. The solvent is subsequently removed in a high vacuum.

Yield: quantitative
$^{31}$P-NMR $(CDCl_3)$:29.1 ppm (s)

D) Use examples

1) Hydrogenation of 2-(3-benzyl-phenyl)-propenoic acid

A solution of 1 g of 2-(3-benzyl-phenyl)-propenoic acid and 460 mg of triethylamine in 15 ml of degassed methanol is admixed while excluding air with 42.3 mg of the catalyst prepared in Example C2). Hydrogenation is subsequently carried out for 72 hours at 90 atm at room temperature.

Yield: quantitative
Enantiomeric excess: 88%

(The determination of the enantiomeric excess is carried out, after oxidation to 2-(3-benzoyl-phenyl)-propionic acid, by HPLC on a chiral phase as described in EP-A-529 444. The preparation of the starting material is likewise described in EP-A-529 444.)

2) Hydrogenation of methyl acetoacetate

A solution of 820 mg of methyl acetoacetate in 15 ml of degassed methanol/methylene chloride 1:1 is admixed while excluding air with 33.8 mg of the catalyst prepared in Example C1). Hydrogenation is subsequently carried out for 72 hours at 90 atm at room temperature.

Yield: quantitative
Enantiomeric excess: 97%

(The determination of the enantiomeric excess is carried out via formation of the Mosher ester and subsequent analysis by gas chromatography.)

What is claimed is:

1. An enantiomerically pure bisphosphines of the general formula (I)

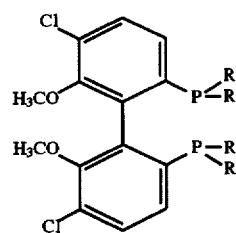

where
R in each case represents a phenyl group which in turn can be substituted by from 1 to 3 substituents from the group $OR^1$, $R^1$, nitro, $NH_2$, $NHR^1$ or $NR_2^1$, where $R^1$ is an alkyl group having up to 6 carbon atoms, or
R is an alkyl group having up to 7 carbon atoms or a cycloalkyl group having from 3 to 7 carbon atoms.

2. A bisphosphine according to claim 1, where
R in each case represents a phenyl group which in turn can be substituted by from 1 to 3 substituents from the group $OR^1$, $R^1$, nitro, $NH_2$, $NHR^1$ or $NR_1^1$, where $R^1$ is an alkyl group having up to 4 carbon atoms, or
R is an alkyl group having 1 to 4 carbon atoms or a cycloalkyl group having 5 or 6 carbon atoms.

3. A bisphosphine according to claim 1, where
R represents phenyl.

4. A process for preparing a bisphosphine of generic formula (I) according to claim 1, said process comprising the steps of:

1. preparing a compound of generic formula (III)

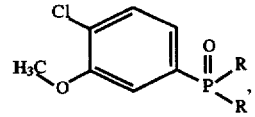

wherein R is defined in claim 1,
by either:
a)
   i) selectively reacting 5-Br-2-Cl anisole with magnesium under Grignard conditions to form the corresponding magnesium bromide Grignard reagent; and
   ii) reacting the Grignard reagent formed in step a)i) with phosphorous oxychloride of the generic formula (II)

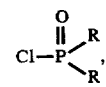

wherein R is defined above,
to give a compound of generic formula (III); or
b)
   i) selectively reacting 5-Br-2-Cl anisole with magnesium under Grignard conditions to form the magnesium bromide Grignard reagent;
and
   ii) reacting the Grignard reagent formed in step b)i) with phosphinic chlorides of generic formula (VI)

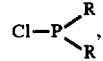

wherein R is defined above,
and subsequently oxidizing the product thus formed to give a compound of generic formula (III);

2. metallating compounds of formula generic (III) in the 6-position followed by reaction with iodine to give a compound of generic formula (IV)

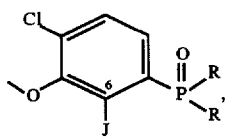

where R is defined above;

3. dimerizing the compounds of generic formula (IV) to give racemic compounds of generic formula (V)

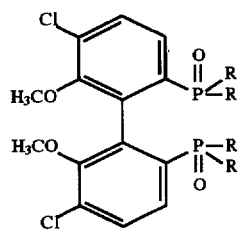

where R is defined above;

4. resolving compounds of formula (V) into their enantiomers by crystallization with enantiomerically pure monocarboxylic or dicarboxylic acids and reducing the enantiomers thus formed to give compounds of generic formula (I).

5. The process according to claim 4, wherein after converting the 5-Br-2-Cl-anisole into the magnesium bromide Grignard reagent, the Grignard reagent is reacted with phosphorous oxychlorides of generic formula (II)

to yield compounds of generic formula (III) the compounds of generic formula (III) are then metallated in the 6-position using a lithium amide and a then subsequently reacted with iodine to give the compounds of generic formula (IV); the compounds of generic formula (IV) are then dimerized by means of an Ullmann coupling to yield racemic compounds of general formula (V) and the phosphine oxides thus obtained are resolved into their enantiomers by crystallization with enantiomerically pure tartaric acids; and these resolved enantiomers are then reduced to the compounds of general formula (I).

6. A method of using bisphosphines of generic formula (I) according to claim 1 for preparing complexes with a metal of group VIII.

* * * * *

UNITED STATES PATENT AND TRADEMARK OFFICE
CERTIFICATE OF CORRECTION

PATENT NO. : 5,710,339
DATED : January 20, 1998
INVENTOR(S) : Laue, et al.

It is certified that error appears in the above-indentified patent and that said Letters Patent is hereby corrected as shown below:

Col. 2, line 30   Delete " 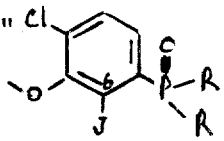 " and substitute

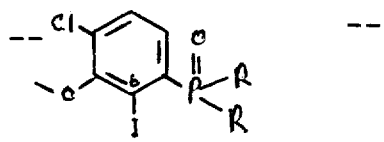 --

Col. 11, line 5   Delete " 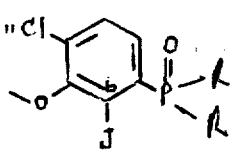 " and substitute

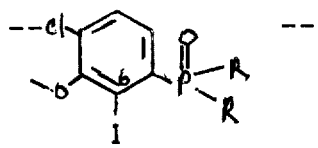 --

Signed and Sealed this

Third Day of November, 1998

Attest:

BRUCE LEHMAN

Attesting Officer

Commissioner of Patents and Trademarks